United States Patent
Dias et al.

(10) Patent No.: US 8,133,580 B2
(45) Date of Patent: Mar. 13, 2012

(54) COATING COMPOSITION FOR A URINARY CATHETER

(75) Inventors: Aylvin Jorge Angelo Athanasius Dias, Maastricht (NL); Guido Joseph Elisabeth Hensen, Oirsbeek (NL); Johannes Wilhelmus Belt, Geleen (NL); Marnix Rooijmans, Born (NL); Nicolaes Hubertus Maria De Bont, Stein (NL); Edwin Peter Kennedy Currie, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 770 days.

(21) Appl. No.: 12/096,623

(22) PCT Filed: Dec. 11, 2006

(86) PCT No.: PCT/EP2006/011902
§ 371 (c)(1),
(2), (4) Date: Oct. 28, 2008

(87) PCT Pub. No.: WO2007/065720
PCT Pub. Date: Jun. 14, 2007

(65) Prior Publication Data
US 2009/0155575 A1   Jun. 18, 2009

(30) Foreign Application Priority Data

Dec. 9, 2005 (EP) .................................... 05111906
Jun. 1, 2006 (EP) .................................... 06011433
Sep. 13, 2006 (EP) .................................... 06019147

(51) Int. Cl.
*B32B 27/08* (2006.01)
*B32B 9/04* (2006.01)

(52) U.S. Cl. ........ 428/335; 424/422; 424/423; 424/426; 435/404; 435/459; 514/13.2; 514/13.6; 514/16.4; 604/265

(58) Field of Classification Search .................. 424/422, 424/423, 426, 335; 435/404, 459; 514/13.2, 514/13.6, 16.4; 604/265
See application file for complete search history.

(56) References Cited

U.S. PATENT DOCUMENTS

| | | |
|---|---|---|
| 5,700,559 A | 12/1997 | Sheu et al. |
| 6,238,799 B1 | 5/2001 | Opolski |
| 2001/0027299 A1 | 10/2001 | Yang et al. |
| 2002/0013549 A1 | 1/2002 | Zhong et al. |

FOREIGN PATENT DOCUMENTS

| | | |
|---|---|---|
| EP | 0 289 996 | 11/1988 |
| WO | 01/51103 | 7/2001 |
| WO | 2004/056909 | 7/2004 |

OTHER PUBLICATIONS

International Search Report for PCT/EP2006/011902, mailed Aug. 6, 2007.
Written Opinion of the International Searching Authority for PCT/EP2006/011902, mailed Aug. 6, 2007.

*Primary Examiner* — Terressa Boykin
(74) *Attorney, Agent, or Firm* — Nixon & Vanderhye P.C.

(57) ABSTRACT

The invention relates to an article comprising a coating, which coating comprises at least two layers, of which the inner layer is a primer layer, comprising a supporting polymer network which is composed of a supporting polymer selected from the group consisting of polyethers and polythioethers, including copolymers thereof, the supporting network optionally comprising a functional non-ionic hydrophilic polymer entangled in the supporting polymer network; and the outer layer is a functional layer comprising a functional non-ionic hydrophilic polymer and a polyelectrolyte.

22 Claims, No Drawings

COATING COMPOSITION FOR A URINARY CATHETER

This application is the U.S. national phase of International Application No. PCT/EP2006/011902, filed 11 Dec. 2006, which designated the U.S. and claims priority to Europe Application Nos. 05111906.3, filed 9 Dec. 2005; 06011433.7, filed 1 Jun. 2006; and 06019147.5, filed 13 Sep. 2006, respectively, the entire contents of each of which are hereby incorporated by reference.

This invention relates to a coated article, a primer composition for coating an article, a functional coating composition for coating an article and a method of coating an article.

Articles may be provided with a coating to impart certain functional properties to the surface thereof. For instance, a hydrophobic surface may be made hydrophilic by applying a hydrophilic coating to it. A hydrophilic coating may simply consist of a layer of molecules such as hydrophilic polymers that provide the desired hydrophilic properties. A recurrent problem is that such single polymer coatings do not adhere to the surface well enough to resist mechanical or other abrasive forces applied to the surface. A common way of making coatings adhere better to the surface is to add chemically reactive groups to the polymers that can be covalently attached to the surface. However, the polymers often easily loose their functional properties when cross-linked to the surface in that way. Also, such coatings generally are not adhered well enough to the surface for particular high-duty applications.

Alternatively functional polymers may be physically entrapped into a network of a second supporting polymer that provides the necessary adherence to the surface. In that way the functional properties of the functional polymer are mostly maintained better. These coatings are often referred to as interpenetrating networks or IPNs. IPNs thus consist of a first functional polymer that provides the desired properties to the coating and a supporting polymer that is chemically cross-linked in order to form a network of polymers. An inherent disadvantage of having the functional polymer physically entrapped in the network rather than covalently coupled to the surface is that the functional polymer may migrate out of the IPN into the environment of the coating. Molecules that may leak out of a particular matrix under particular circumstances are known in the art by the term "migrateables". The term is synonymous with "extractables" or "extractable components" which are also frequently used in the art.

In particular in applications wherein a coating may come into contact with a liquid, it is desired that the amount of migrateables is as low as possible. For example, coatings used in membranes for separations and films for food contact should contain a minimal amount of migrateables. The desire to reduce the amount of migrateables becomes especially pertinent when the coatings are applied to an article used in a sensitive application such as in a medical applications. Examples of such articles include medical devices that come into close contact with the body or body fluids such as contact lenses, guide wires and catheters. The loss of one or more components from a coating may result in change in composition and functional properties of the coating. Also contaminating the immediate host environment may be a problem. Moreover, the migrateable component may be harmful when released into the environment of the coating, such as the food, human body or body fluid.

A number of ways have been described to reduce the migration of polymers out of an IPN coating. One proposed solution is to increase the cross-link density of the supporting polymer, thus resulting in a network with smaller meshes. Increasing the cross-link density of the supporting polymer, however, may result in a brittle coating and/or failure of other mechanical requirements.

Another suggested solution (U.S. Pat. No. 4,642,267 and U.S. Pat. No. 5,700,559) is to increase the molecular interaction between the cross-linked supporting polymer and the non-cross-linked functional polymer via Van der Waals, hydrogen bonding or electrostatic interactions. However, these methods do not result in sufficient reduction of the amount of migrateables, in particular when the coating is subjected to repeated mechanical perturbation, dramatic temperature changes, solvents, electrolytes, solutions that interfere with the polymer—polymer interactions or circumstances that cause a dramatic swell of the IPN (Leger et al. Micromolecules 1995, 28, 143, J. E Mark et. al. J. Polym. Sci. Polym. Phys. Ed. (1983), 21 1971).

Another solution (U.S. Pat. No. 6,224,893) to better entrap the functional polymer in the network is to introduce cross-links between the functional polymers. In that way two intercalating networks (one consisting of the supporting polymer and the other of the functional polymer) are formed that are not chemically attached to each other. Such networks are often referred to as total interpenetrating networks or total IPNs. The chemical procedures involved in making such total IPNs are often complicated and cumbersome, and involve the addition of cross-linkable groups to the functional polymer. A total IPN may provide excellent coatings with a low amount of migrateables, however, it is difficult to achieve due to phase separation, that arises due to differences in polymerization speed of the ingredients or inadequate compatibility between the two networks. Compatibility in this respect refers to the ability of the two polymers to achieve a desired function.

Yet another solution to prevent the functional polymer from migrating out of a lubricious coating consisting of a supporting polymer and a hydrophilic polymer is provided in U.S. Pat. No. 6,238,799. Herein it is suggested to attach reactive groups to the functional polymer, which react into the network of the supporting polymer. It is said that such covalent anchoring may be suitably used with functional polymers that have been polymerized with reactive monomers, such as PVP/RCOOH, PVP or PVOH anhydrides or PVP acetamide. In that way a coating is obtained wherein the functional polymer is chemically cross-linked to the supporting polymer forming the network. However, in this procedure a reactive group has to be attached to the functional polymer via a prior chemical reaction. Moreover, the restriction of the mobility of the functional polymer is said to adversely affect the functional properties of the coating.

Yet another solution has been suggested in WO99/64086 wherein a steel stent is coated with a supporting polymer (polydimethylsiloxane) that has been chemically functionalised with benzophenone, a Norrish type II photoinitiator. After drying of the supporting polymer, a functional polymer (PVP) is then UV cross-linked to the network through hydrogen abstraction.

Photochemical surface modification by Norrish Type II hydrogen abstraction reactions has been applied in U.S. Pat. No. 5,002,583. The approach described therein requires an additional synthetic step wherein the hydrophilic polymers and biopolymers are modified with a Norrish Type II chromophore (typically diarylketones) prior to grafting onto a surface.

Still, the above-mentioned solutions do not provide entirely satisfactory results, in the sense that they often do not combine the desired ease of handling with a sufficient reduction of the amount of migrateables in order to allow the coatings to be used in applications where low amount of migrateables is desired, such as in the human body.

It is generally desired to provide an article with a coating having a high lubricity and high wear resistance, having a good physical appearance and being biocompatible. At the same time it is generally desired that the coating comprises as little as possible migrateables. It is also desired to minimise the release of coating particulates from the coating when the coating is exposed to friction. Also it is generally desired that the thickness is as low as possible and that the coating comprises as few as possible coating defects. One problem underlying the present invention is how to provide a coating meeting all these requirements.

It is an object of the present invention to provide a novel article, comprising a coating which may be used as an alternative to a known article.

It is in particular an object to provide a novel article comprising a hydrophilic coating wherein one or more of the above identified objections are overcome.

It is a further object to provide a coated article comprising a functional coating with one or more of the following characteristics: lubricity (after wetting), good wear-resistance, satisfactory dry-out time (after wetting), satisfactory adherence of the coating and satisfactory low level of (polymeric) migratables.

It is further an object to provide a method for preparing a coated article.

It is a further object to provide a coating composition, in particular a primer composition and/or a functional coating composition, for providing an article with a coating.

One or more other objects that may be solved in accordance with the present invention will become apparent from the description, below.

It has now been found possible to solve one or more objects by providing an article with a specific coating comprising a primer layer and a functional layer.

Accordingly, the present invention relates to an article—in particular a medical device, more in particular a catheter—comprising a coating, which coating comprises at least two layers, of which two layers:

the inner layer (i.e. a layer between the outer layer and the surface) is a primer layer, comprising a supporting polymer network which is composed of a supporting polymer selected from the group consisting of polyethers and polythioethers, including copolymers comprising a polyether and/or polythioether moiety, the supporting network optionally comprising a functional non-ionic hydrophilic polymer which may be partially or fully entangled in the supporting polymer network; and the outer layer is a functional layer comprising a functional non-ionic hydrophilic polymer (other than an ionomer) and a polyelectrolyte (which may be an ionomer). The hydrophilic polymer and/or ionomer molecules may advantageously be chemically coupled (crosslinked and/or grafted) to each other and/or the primer layer.

The term polymer is used herein for a molecule comprising two or more repeating units. In particular it may be composed of two or more monomers which may be the same or different. As used herein, the term includes oligomers and prepolymers. Usually polymers have a number average weight of about 500 g/mol or more, in particular of about 1000 g/mol or more, although the molecular weight may be lower in case the polymer is composed of relatively small monomeric units.

In line with common practice, when referred to "a" moiety or "the" moiety (e.g. a compound for instance a (hydrophilic) polymer, a polyelectrolyte, an initiator) this is meant to refer to one or more species of said moiety.

The article may in particular be selected from the group consisting of catheters, endoscopes and laryngoscopes, tubes for feeding or drainage or endotracheal use, guide wires, condoms, barrier coatings (e.g. for gloves, wound dressings, contact lenses, implants, extracorporeal blood conduits), membranes (e.g. for dialysis, blood filters, devices for circulatory assistance), more in particular an article selected from the group consisting of catheters, even more in particular from urinary catheters. The coating can also be applied to the following non-medical articles; packaging for foodstuff, razor blades, fishermen's nets, conduits for wiring, water pipes having a coating inside, water slides, sports articles, cosmetic additives, mould release agents, and fishing lines and nets.

It has in particular been found that in accordance with the invention a coating is provided that is lubricious after wetting the coating with water, a coating that shows a satisfactory or even advantageous adherence to the surface of the article, a coating that is essentially free of visible cracks and/or that has a satisfactory or even advantageous dry-out time.

The term "wetted" is generally known in the art and—in a broad sense—means "containing water". In particular the term is used herein to describe a coating that contains sufficient water to be lubricious. In terms of the water concentration, usually a wetted coating contains at least 10 wt % of water, based on the dry weight of the coating, preferably at least 50 wt %, based on the dry weight of the coating, more preferably at least 100 wt % based on the dry weight of the coating. For instance, in a particular embodiment of the invention a water uptake of about 300-500 wt % water is feasible.

Within the context of the invention a coating on the (outer) surface of a medical device, such as a catheter, is considered lubricious if it can be inserted into the intended body part without leading to injuries and/or causing unacceptable levels of pain to the subject. In particular, a coating is considered lubricious if it has a friction as measured on a Harland FTS Friction Tester of 20 g or less at a clamp-force of 300 g and a pull speed of 1 cm/s, preferably of 15 g or less, using the following settings:

The lubricity can be determined using a Harland FTS5000 Friction Tester (HFT) or equivalent friction tester. The protocol is as indicated in the following table:

TABLE

| HFL settings | |
|---|---|
| Transport movement (cm) | 10 |
| clamp force (g) | 300 |
| pull speed (cm/s) | 1 |
| acceleration time (s) | 2 |
| number of rubs | 25 |

Friction tester pads from Harland Medical Systems can be used: P/N 102692, FTS5000 Friction Tester Pads, 0.125" 0.5" 0.125" 60 durometer.

Subsequently insert the desired test description when "run test" is activated. After inserting the Mandril into the article (in particular a catheter) place the article in the holder. Adjust the device down to the desired position such that the article is soaked in the wetting liquid for 1 min. After zero gauging in water, activate the protocol. Remove the holder from the force gauge and subsequently the remove the article from the holder.

Within the context of the invention, the dry-out time is the duration of the coating remaining lubricious after the device has been taken out of the wetting fluid wherein it has been stored and/or wetted. Dry-out time can be determined by measuring the friction in grams as a function of time the catheter had been exposed to air on the HFT (see above). The dry-out time is the point in time wherein the friction reaches a value of 20 g or higher, or in a stricter test 15 g or higher, as measured at a temperature of 22° C. and 35% relative humidity.

The primer layer generally contributes to the adherence of the functional polymer, in particular if the surface of the article provided with the coating is more hydrophobic than the functional polymer. Examples of suitable surfaces are for instance surfaces that consist of metals, polymers—especially plastics—and ceramics. A preferred example of a suitable polymer is polyvinylchloride. Other particularly suitable materials include silicon polymers, polyamides (e.g. Nylons) and poly-urethanes, including copolymers of such polymers, for instance a copolymer of a polyamide and a polyether (e.g. Pebax™).

A suitable supporting polymer for use in the invention comprises functional moieties capable of undergoing cross-linking reactions. When crosslinked at the functional moieties, the supporting polymer is usually capable of forming a three-dimensional network, wherein another polymer may become entangled. The functional moiety of the polymer may be selected from the group consisting of radically reactive groups, such as amino, amido, sulphhydryl (SH), unsaturated esters, ethers and amides, alkyd/dry resins and alkene groups, in particular vinyl groups.

The average number of reactive groups per molecule of the supporting polymer (before cross-linking) should be more than 1 in order to form a cross-linked network. Preferably it is at least 1.2, more preferably at least 1.5, in particular at least 2.0. Preferably the average number of groups is up to 64, more preferably up to 15, in particular up to 8.

The primer layer optionally comprises a functional non-ionic hydrophilic polymer. It is contemplated that this helps to improve adherence of the functional layer to the primer layer, and thus to the article. The functional non-ionic hydrophilic polymer in the primer layer may be the same or different as in the functional layer. A hydrophilic polymer is in particular a polymer that is water-soluble, capable to bind or hold a relatively large amount of water (for instance because it is water-gellable and/or water swellable). With respect to the capability to hold a large amount of water: the amount is in particular considered large if its water uptake capacity at 25° C. is at least about 25% of the weight of the polymer, more in particular at least about 50% of the weight of the polymer, more in particular at least about 100% of the weight of the polymer.

In particular, the functional non-ionic hydrophilic polymer in the outer layer is lubricious when wetted with a sufficient amount of water.

The supporting polymer comprises polyether and/or polythioether moieties. Preferably the supporting polymer further comprises double carbon-carbon bonds, which can be used to cross-link the polymer. Preferably the polyether/polythioether moiety (moiety a1) is linked with at least two moieties (moiety a3) comprising a double carbon-carbon bond—in particular a hydroxyacrylate or a hydroxymethacrylate which may comprise an alkyl side group. Preferably the link is realised by carbamate groups (i.e. —(NR)—(C=O)—O—, wherein R is hydrogen or an alkyl). Herein the carbamate may in particular originate from a di-isocyanate and alcohol. Other links that are envisaged, are in particular a thiocarbamate or a carbamate, ester, amide and an ether.

In particular preferred is a supporting polymer selected from the group consisting of polymers composed of at least a1) a polyether or polythioether; and/or a2) a moiety comprising at least two isocyanates; and/or a3) a hydroxyalkylacrylate, a hydroxyalkylmethacrylate, a polyhydroxyalkylacrylate and a polyhydroxymethacrylate.

Moiety a1) is preferably selected from polyalkylene glycoles (such as PEG and PPG and combinations thereof) and polytetrahydrofuran. More preferably it is a copolymer of poly(-methyl-1,4-butanediol) and tetramethyleneglycol. Particularly preferred is poly(-methyl-1,4-butanediol)(tetramethyleneglycol) (PTGL). Such polymer is available from Hodogaya (as poly(2-methyl-1,4-butanediol)alt(tetramethyleneglycol).

In particular suitable examples of moiety a2) are 2,4-tolylene diisocyanate, 2,6-tolylene diisocyanate, 1,3-xylylene diisocyanate, 1,4-xylylene diisocyanate, 1,5-naphthalene diisocyanate, m-phenylene diisocyanate, p-phenylene diisocyanate, 3,3'-dimethyl-4,4'-diphenylmethane diisocyanate, 4,4'-diphenylmethane diisocyanate, 3,3'-dimethylphenylene diisocyanate, 4,4'-biphenylene diisocyanate, 1,6-hexane diisocyanate, isophorone diisocyanate, methylenebis(4-cyclohexylisocyanate), 2,2,4-trimethylhexamethylene diisocyanate, bis(2-isocyanatethyl)fumarate, 6-isopropyl-1,3-phenyl diisocyanate, 4-diphenylpropane diisocyanate, hydrogenated diphenylmethane diisocyanate, hydrogenated xylylene diisocyanate, tetramethyl xylylene diisocyanate, lysine isocyanate, and the like. Moiety a2 is preferably selected from toluene diisocyanate and 4-cyclohexyldiisocyanate.

Moiety a3) is preferably selected from hydroxyalkylacrylate and hydroxyalkylmethacrylate. Herein the alkyl is preferably a C1-18 alkyl. More preferably the alkyl is C2-C7, in view of the hydrophilic properties of the (meth)acrylate groups. Good results have been achieved with a compound wherein the alkyl is ethyl.

The supporting polymer (in a non-crosslinked state) usually has a number average molecular weight (Mn) as determinable by size exclusion chromatography in tetrahydrofuran using polystyrene standards, of at least 300 g/mol, in particular at least 400 g/mol, more in particular at least 500 g/mol, preferably at least 750 g/mol more preferably at least 1000 g/mol. Usually the molecular weight is about 20000 g/mol or less, in particular 10000 g/mol or less, more in particular 5000 g/mol or less, preferably 3000 g/mol or less, in particular about 2500 g/mol or less.

The concentration of the supporting polymer in the primer layer is usually at least 65 wt %, based on the dry weight of the layer (i.e. without solvent). For improved adherence, the concentration is preferably at least 70 wt %, in particular at least 75 wt %, more in particular at least 80 wt %.

The upper limit is mainly determined by the desired concentration of on ore more other components which may be present. In particular the concentration may be up to 100 wt %, more in particular up to 95 wt %, based on the total dry weight of the layer. Good results have in particular be realised with a coating wherein the supporting polymer concentration is up to 90 wt %, based on the total dry weight of the layer.

The functional non-ionic hydrophilic polymer b) is preferably selected from the group consisting of polylactams, polyalkylene oxides, in particular polyethylene oxides and polypropylene oxides, poly vinyl alcohols, polyacrylates, polyhydroxyalkylates, in particular polyhydroxyethylacrylate, polymethacrylates, polyhydroxymethacrylates, in particular polyhydroxyethylacrylates, and polyacrylamides. Particularly good results have been achieved with polyvinylpyrrolidones.

It has been found that adherence between the primer layer and the surface of the article and/or the primer layer and the outer layer is improved with increasing molecular weight of the functional non-ionic hydrophilic polymer. Accordingly the weight average molecular weight of the functional non-ionic hydrophilic polymer, as determinable by as determined by light scattering, optionally in combination with size exclusion chromatography, is usually at least 20 kg/mol, in particular at least 55 kg/mol, preferably at least 250 kg/mol, in particular at least 360 kg/mol, more preferably at least 500 kg/mol, in particular at least 750 kg/mol.

For practical reasons (ease of application and/or ease to realise uniform coating thickness) the weight average molecular weight (Mw) is usually up to 10 million, preferably up to 5 million g/mol, more preferably up to 3 million g/mol, most preferably up to 2 million g/mol, in particular up to 1.5 million g/mol, more in particular up to 1.3 million g/mol, even more in particular up to 1 million g/mol.

In particular polyvinylpyrollidone (PVP) and polyethyleneoxide (PEO) having an Mw of at least 100000 g/mol have been found to have a particular positive effect on lubricity and a low tendency to migrate out of the coating.

In particular for polyvinylpyrrolidone (PVP) and polymers of the same class, a polymer having a molecular weight corresponding to at least K15, more in particular K30, even more in particular K80 is preferred. Particular good results have been achieved with a polymer having a molecular weight corresponding to at least K90. Regarding the upper limit, a K120 or less, in particular a K100 is preferred. The K-value is the value as determinable by the Method W1307, Revision 5/2001 of the Viscotek Y501 automated relative viscometer. This manual may be found at www.ispcorp.com/products/hairscin/index3.html If present, the concentration of the functional non-ionic hydrophilic polymer in the primer layer is usually at least 1 wt %, in particular at least 3 wt %, more in particular at least 5 wt % based on the total dry weight of the coating. Usually the concentration is up to 65 wt, preferably up to 50 wt %, more preferably up to 40 wt %, most preferably up to 30 wt %, in particular up to 20 wt %, more in particular up to 15 wt %, even more in particular up to 10 wt %. Suitably it may in particular be chosen in the range of 1 to 99 wt %, in particular 1-65 wt %, more in particular 1-40 wt %, preferably 1-30 wt %, more preferably 3-20 wt %, most preferably 5 to 10 wt %, based on the total dry weight of the coating.

The primer layer may suitably be applied on the article in a manner known per se. Preferably a primer composition according to the invention is used. Such composition has been found to result in a coating with advantageous properties.

A primer composition for providing an article with a primer layer according to the invention typically comprises
a) the supporting polymer (as identified above and/or in the claims), in a total concentration of 1-60 wt % in particular 1-20 wt %, based on the total weight of the composition
b) optionally a functional non-ionic hydrophilic polymer (as identified above and/or in the claims) in a total concentration of up to 30 wt %, preferably up to 15 wt %, based on the total weight of the composition;
c) a Norrish I type photoinitiator.

Typically said components, and optional one or more additives such as an antioxidant, an alicyclic compound, an aliphatic compound, an antioxidant and/or one or more additives known in the art to be suitable for use in a primer composition, are dissolved in a suitable amount of solvent. In particular the solvent concentration may be at least 68 wt %, more in particular at least 75 wt %, preferably at least 80 wt %, more preferably at least 85 wt. %, even more preferably at least 90 wt % of a solvent. In view of handling properties (low viscosity) and/or in order to facilitate the application of the composition such that a coating with the desired thickness is obtained, the total solids content is preferably 30 or less, more preferably 20 or less, even more preferably 15 wt % or less, in particular 10 wt % or less.

The solvent may be a single solvent or a mixture of solvents. It is chosen such that the polymers can be dissolved or at least dispersed therein.

Preferably the comprises an organic solvent having a boiling point below 140° C., in particular of 120° C. or less, more in particular of 100° C. or less. This may facilitate drying of the coating, if desired, especially if one or more further additives are present with a relatively low boiling point. Preferably the organic solvent is an alcohol, in particular a monohydric alcohol, more preferably methanol and/or ethanol. It has been found advantageous to include some water in the solvent, in particular in an amount that is soluble in the solvent, such as in a polar alcohol, in particular a C1-C4 monohydric alcohol. The water concentration may be at least 1 wt % based on the weight of the solvent in particular at least 2 wt %, more in particular at least 4 wt %, based on the total weight of the solvent. In view of dissolving/dispersing the supporting polymer, the water content is usually relatively low compared to the content of organic solvent, e.g. 10 wt % or less. It has been found that the presence of water facilitates dissolving the components into the solvent.

A preferred primer composition of the invention comprises
a) at least 2 or at least 3 wt. % and/or up to 10 wt %, in particular up to 8 wt % of the supporting polymer, more preferably 2-8 wt %, in particular 3-8 wt. % of the supporting polymer;
b) at least 0.3, 0.4 or 0.5, and/or up to 20, 15 wt %, or 10 wt % of the functional polymer, in particular 0.3-20 wt %, preferably 0.4-10 wt %, more preferably 0.5-3 wt %, in particular 0.5-1.0 wt %, for instance about 0.5 or 0.75 wt % of the functional polymer based on the total weight of the primer composition.

The concentration of the initiator c) can be determined based upon the efficiency of the initiator, the desired curing rate and the amount of polymerizing components (typically component a)).

Usually, the total concentration of the initiator c) is up to 10 wt %, based on the weight of components a) and b), in particular 0.5-8 wt % more in particular 1-6 wt %, preferably 2-6, more preferably 2-5 wt % based on the weight of components a) and b).

A suitable photoinitiator for use in the invention is a compound capable of performing a photochemical Norrish type I cleavage reaction or other photochemical homolytic bond cleavage. Photoinitiated polymerisation can be initiated by two types of photoinitiators. Norrish Type I photoinitiators, which occur by homolytic cleavage of the chromophore directly to generate radicals that initiate polymerization and Norrish Type II photoinitiators that generate radicals indirectly by hydrogen abstraction from a suitable synergist, e.g. a tertiary amine. More in detail: free-radical photoinitiators are generally divided into two classes according to the process by which the initiating radicals are formed. Compounds that undergo unimolecular bond cleavage upon irradiation are termed Norrish Type I or homolytic photoinitiators, as shown by formula (1):

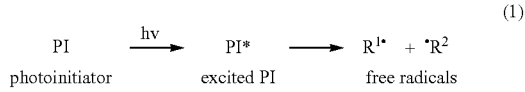

Depending on the nature of the functional group and its location in the molecule relative to the carbonyl group, the fragmentation can take place at a bond adjacent to the carbonyl group (α-cleavage), at a bond in the β-position (β-cleavage) or, in the case of particularly weak bonds (like C—S bonds or O—O bonds), elsewhere at a remote position. The most important fragmentation in photoinitiator molecules is the α-cleavage of the carbon-carbon bond between the carbonyl group and the alkyl residue in alkyl aryl ketones, which is known as the Norrish Type I reaction.

If the excited state photoinitiator interacts with a second molecule (a coinitiator COI) to generate radicals in a bimolecular reaction as shown by formula (2), the initiating system is termed a Type II photoinitiator. In general, the two main reaction pathways for Type II photoinitiators are hydrogen abstraction by the excited initiator or photoinduced electron transfer, followed by fragmentation. Bimolecular hydrogen abstraction is a typical reaction of diaryl ketones. Photoinduced electron transfer is a more general process, which is not limited to a certain class of compounds.

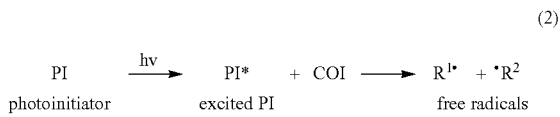

(2)

Examples of suitable Type I or cleavage free-radical photoinitiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Commercial examples of suitable Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly {2-hydroxy-2-methyl-1-[4-(1-methylvinyl)phenyl]propan-1-one}, Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethyl-benzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), and the like. Also mixtures of type I photoinitiators can be used. For colored (e.g. pigmented) systems, phosphine oxide type photoinitiators and Irgacure 907 are preferred.

The article may be provided with the primer composition in any way to provide a layer, e.g. by dipping or spraying, of a suitable thickness.

For improved wear resistance and/or a relatively short curing time it is preferred that the primer composition is applied in a relatively thin layer, in particular in an amount to provide a final layer thickness of 20 μm or less, more in particular of 7 μm or less, preferably of 5 μm or less, more preferably of 3 μm or less.

The thickness of the primer layer may be at least 0.1 μm, 0.2 μm, 0.3 μm, or 0.5 μm.

When the primer composition has been applied to the surface it may be cured in any suitable way for the particular initiator and polymer combination.

The functional outer layer comprises a functional non-ionic hydrophilic polymer.

In view of lubricity and/or dry-out properties, the concentration of the functional non-ionic hydrophilic polymer in the functional layer is preferably at least 25 wt %, in particular at least 40 wt %, more preferably at least 50 wt %, in particular at least 60 wt %, even more preferably at least 65 wt %, in particular at least 70 wt %, based on the total dry weight of the layer.

The upper limit is in particular determined by the one or more other components that are present. In particular the concentration may be up to 99 wt %, preferably up to 95 wt % in particular up to 90 wt %, based on the total dry weight of the layer. In particular in case a high dry-out time is desired (for which purpose a relatively high amount of polyelectrolyte and/or one or more other additives may be present), the concentration may be 80 wt % or less, 70 wt % or less, 60 wt % or less, or even 25 wt % or less.

Suitable and preferred hydrophilic polymers and molecular weights are further as identified elsewhere in the present document, when describing the primer layer.

The presence of a polyelectrolyte, in addition to a non-ionic hydrophilic polymer is in particular found advantageous with respect to a relatively high dry-out time of the wetted coating. It has further been found that the water uptake rate is increased in a coating of the invention comprising a polyelectrolyte, compared to a similar coating without the polyelectrolyte. This is in particular advantageous in case the article is stored with a dried coating and the coating is to be wetted prior to use. Satisfactory wetting of a coating, for instance of a catheter, may thus be accomplished within a few seconds after submersion in water or exposure to air with a relative humidity of 100%.

Herein a polyelectrolyte is understood to be a compound comprising a plurality of charges (when dissolved in water). In principle it may be a low molecular weight compound. Good results have been achieved with a polymeric electrolyte, which may also be referred to as an ionomer. The ionomer may be a linear, branched or crosslinked polymer or oligomer composed of macromolecules comprising constitutional units. In particular a polymer is considered a ionomer, in case between 5 and 100% of the constitutional units contain ionic or ionizable groups, or both. Herein a constitutional unit is understood to be for example a repeating unit, for example a monomer. A polyelectrolyte herein may refer to one type of polyelectrolyte composed of one type of macromolecules, but it may also refer to two or more different types of polyelectrolytes composed of different types of macromolecules.

Considerations when selecting a suitable polyelectrolyte are its solubility and viscosity in aqueous media, its molecular weight, its charge density, its affinity with the supporting network of the coating and its biocompatibility. Herein biocompatibility means biological compatibility by not producing a toxic, injurious or immunological response in living mammalian tissue.

Examples of ionic or ionizable groups that may be present in the polyelectrolyte are primary, secondary and tertiary amine groups, primary, secondary, tertiary and quarternary ammonium, phosphonium and sulfonium groups, carboxylic acid groups, carboxylate groups, sulfonic acid groups, sulfate groups, sulfinic acid groups, sulfinic groups, phosphinic acid groups and phosphate groups. Such groups are very effective in binding water. In one embodiment of the invention the polyelectrolyte also comprises metal ions. Metal ions, when dissolved in water, are complexed with water molecules to form aqua ions $[M(H_2O)_x]^{n+}$, wherein x is the coordination number and n the charge of the metal ion, and are therefore particularly effective in binding water. Metal ions that may be present in the polyelectrolyte are for example alkali metal ions, such as $Na^+$ or $K^+$. In another embodiment of the invention, in particular when the polyelectrolyte comprises quarternary ammonium groups, anions are present. Such anions can for example be halogenides, such as $Cl^-$, $Br^-$, $I^-$ and $F^-$, and also sulphates, nitrates, carbonates and phosphates.

Suitable polyelectrolytes include homo- and co-polymers of acrylic acid, methacrylic acid, acrylamide, maleic acid, fumaric acid, monomers comprising sulfonic acid, monomers comprising quarternary ammonium salts and mixtures and/or derivatives thereof. Examples of suitable polyelectrolytes are poly(acrylamide-co-acrylic acid) salts, for example poly(acrylamide-co-acrylic acid) sodium salt, poly(acrylamide-co-methacrylic acid) salts, for example poly(acrylamide-co-methacrylic acid) sodium salt, poly(methacrylamide-co-acrylic acid) salts, for example poly(methacrylamide-co-acrylic acid) sodium salt, poly(methacrylamide-co-methacrylic acid) salts, for example poly(methacrylamide-co-methacrylic acid) sodium salt poly(acrylic acid) salts, for example poly(acrylic acid) sodium salt, poly(methacrylic acid) salts, for example poly(methacrylic acid) sodium salt, poly(acrylic acid-co-maleic acid) salts, for example poly(acrylic acid-co-maleic acid) sodium salt, poly(methacrylic acid-co-maleic acid) salts, for example poly(methacrylic acid-co-maleic acid) sodium salt, poly(acrylamide-co-maleic acid) salts, for example poly(acrylamide-co-maleic acid) sodium salt, poly(methacrylamide-co-maleic acid) salts, for example poly(methacrylamide-co-maleic acid) sodium salt, poly(acrylamido-2-methyl-1-propanesulfonic acid) salts, poly(4-styrene sulfonic acid) salts, poly(acrylamide-co-dialkyl ammonium chloride), quaternized poly[bis-(2-chloroethyl)ether-alt-1,3-bis[3-(dimethylamino)propyl]urea], polyallylammonium phosphate, poly(diallyldimethylammonium chloride), poly(sodium trimethyleneoxyethylene sulfonate), poly(dimethyldodecyl(2-acrylamidoethyl)ammonium bromide), poly(2-N methylpyridiniumethylene iodine), polyvinylsulfonic acid salts, and salts of poly(vinyl)pyridines, polyethyleneimines, and polylysines.

Good results have been achieved with a copolymer comprising at least an acrylamide moiety, a acrylic acid moiety (i.e. in acidic form) and an acrylic acid sodium salt moiety. The acrylamide moiety, the acrylic acid moiety and/or the acrylic acid sodium salt may be partially or fully replaced by a methacrylamide acid, methacrylic acid respectively methacrylic acid sodium salt. The sodium salt may be partially or fully replaced by another salt.

The weight to weight ratio [acrylamide moieties+methacrylamide moieties] to [acidic acrylic acid moieties+acidic methacrylic acid moieties+acrylic acid salt moieties+methacrylic acid salt moieties] preferably is 1:10 to 4:1, more preferably 1:5 to 1:3, in particular about 1:4.

Generally, between 5 and 99 wt %, preferably between 50 and 90 mol %, more preferably between 70 and 85 mol % of the total of acrylamide moieties+methacrylamide moieties+acidic acrylic acid moieties+acidic methacrylic acid moieties+acrylic acid salt moieties+methacrylic acid salt moieties comprise ionizable or ionized groups, i.e. are acrylic acid (salt) moieties or methacrylic acid (salt) moieties. In the lubricious coating, i.e. after wetting the hydrophilic coating, said ionizable groups may be ionized or non-ionized. Typically between 1 and 100% of the total amount of ionizable and ionized groups is ionized when the copolymeric polyelectrolyte is in the lubricious coating, preferably between 30 and 100%, more preferably between 50 and 100%, in particular between 60 and 100%.

The presence of a polyelectrolyte, in particular a ionomer, has in particular been found advantageous with respect to the dry-out time of the wetted coating. In addition or alternatively the wetting rate may be improved. In view thereof, the amount of polyelectrolyte, in particular ionomer, is preferably at least 1 wt %, based upon the total dry weight of the composition, in particular at least 5 wt %, more in particular at least 10 wt %.

The polyelectrolyte concentration is usually 75 wt % or less, in particular 50 wt % or less, based upon the dry weight of the layer. In view of reducing or avoiding the risk of crack forming in the (dried coating), which crack formation may be undesirable from an aesthetic viewpoint or give rise to delamination, a concentration of up to 40 wt %, in particular of up to 30 wt %, based on the dry weight of the layer, is preferred. Particularly good results have been achieved with a polyelectrolyte concentration of up to 20 wt %, based on the dry weight of the layer.

For a decreased migrateability, the polyelectrolyte is preferably a polymer. A ionomer in a composition/coating of the invention usually has a weight average molecular weight of at least about 1 kg/mol, as determinable by light scattering, optionally in combination with size exclusion chromatography. A relatively high molecular weight ionomer is preferred for increasing the dry-out time and/or reduced migration out of the coating. The weight average molecular weight of the polyelectrolyte is preferably at least 20 kg/mol, more preferably at least 100 kg/mol, even more preferably at least about 150 kg/mol, in particular about 200 kg/mol or more. For ease of applying the coating it is preferred that the average weight is 1000 kg/mol or less, in particular 500 kg/mol or less, more in particular 300 kg/mol or less.

Further one or more additives may be present, which have a beneficial effect on the lubricity and/or the dry-out time and/or another property of the coating. In particular such additive is selected from the group consisting of water soluble aliphatic compound, water soluble alicyclic compounds and antioxidants.

If present in the functional layer and/or the primer layer, the total concentration of the alicyclic/aliphatic compounds is usually at least 0.5, preferably at least 1.0% in particular at least 3 wt %. It usually is up to 25 wt %, preferably up to 20 wt % in particular up to 15 wt %. Suitable ranges include 0.5 to 25 wt %, preferably 1 to 20 wt % more preferably 3 to 15 wt %, based on the total weight of polymers in said layer.

The alicyclic compound respectively aliphatic compound may in particular be selected from the group consisting of alcohols (in particular polyols), ethers, aldehydes, amides, esters, thiols, thioesters, organic acids and ketones, preferably from saturated aliphatic polyols, saturated aliphatic ethers, saturated aliphatic aldehydes, saturated aliphatic amides, saturated aliphatic esters, saturated aliphatic thiols, saturated aliphatic thioesters, saturated aliphatic organic acids and saturated aliphatic ketones.

An aliphatic/alicyclic compound with a relatively low molecular weight is particularly suitable, such as a compound with a molecular weight of less than 1000 g/mol, more in particular of 800 g/mol or less, preferably of 600 gram/mol or less. The use of a low molecular weight compound may have one or more of the following advantages, compared to a compound having a higher molecular weight. It is contemplated that such a compound is in particular beneficial with respect to lubricity and/or dry out time in case the article is or has been sterilised, with less or no risk of gelling of the coating during sterilisation, compared to a coating comprising a similar compound of a higher molecular weight. It may further offer the advantage of less contamination of the body wherein the article (such as a catheter) may be inserted in the body of a human or other animal. Polymeric compounds tend to stick more to body tissue, such as endothelium, and/or are less easily removed by the body than stabilising compounds having a low molecular weight (such as glycerol), and are thus less likely to cause a harmful effect.

In view of partially or fully avoiding evaporation of the alicyclic or aliphatic compound (e.g. during sterilisation or drying), said compound preferably has a boiling point of more than 50° C., in particular of at least 80° C., preferably of more than 100° C., in particular of more than 140° C. and more in particular of at least 200° C.

Preferred alcohols include alkylene glycols, such as diethyleneglycol, triethyleneglycol, tetraethyleneglycol, propyleneglycol, dipropyleneglycol, triprolyeneglycol, (low molecular) ethoxylated or propoxylated alcohols and/or amines like ethanolamine, diethanolamine, triethanolamine, polyethylene glycol (PEG), in particular polyalkylene glycols having a Mw up to about 600 g/mol lower aliphatic alcohols—in particular C1-C8 alcohols, more in particular C3-C4 alcohol, such as glycerol and isopropanol, 1-propanol and 1-butanol—and combinations thereof. Good results have further been achieved with a carbohydrate, in particular a monosaccharide, more in particular glucose.

Preferred ethers include polyalkylene glycols, such as PEG.

Suitable aldehydes include C1-C8 aldehydes. Preferred aldehydes include formaldehyde, acetaldehyde and butanal.

Suitable ketones include C3-C8 ketones. Preferred ketones include acetone and methylethylketone.

Suitable organic acids include C1-C8 organic acids. Preferred organic acids include formic acid.

An antioxidant has been found to have a beneficial effect on lubricity and/or dry-out time, in particular in case the coated article is sterilized by radiation.

If present, the total concentration of the antioxidant in the functional layer and/or primer layer usually is at least 0.01 wt %, preferably at least 0.02 or at least 0.05 wt %. It usually is up to 2 wt %, in particular up to 1 wt %, more in particular up to 0.5 wt %. Preferably it is in the range of 0.02 to 1 wt %, more preferably 0.05 to 0.5 wt %, based on the total weight of polymers in said layer.

As an antioxidant, in principle any antioxidant may be used, in particular any physiologically allowable antioxidant. An antioxidant is an organic molecule which is capable of preventing or slowing down an oxidation reaction. An antioxidant, as used herein, in general is an organic compound comprising double bonds, in particular a number of conjugated double bonds. Preferably at least one double bound is present in a carbon ring (which may comprise one or more heteroatomes) which contains at least one double bond.

Suitable antioxidants in particular include anti-oxidative vitamins (such as vitamin C and vitamin E) and phenolic antioxidants.

In particular good results have been achieved with an antioxidant that is soluble or at least dispersible in the coating composition at the intended concentration.

Preferred antioxidants include vitamin C (ascorbic acid), alkyl hydroxybenzyl alcohols (such as 5-di-tert-butyl-4-hydroxybenzyl alcohol), alkyl hydroxybenzoic acids (such as 3,5-di-tert-butyl-4-hydroxybenzoic acid) pyrogallol. alkylated hydroxytoluene (such as butylated hydroxy toluene), 2,6-ditertbutyl-4-ethyl-phenol.

Preferred examples of commercially available phenolics include Irganox 1300™, Irganox 1035™, Irganox 1098™, Irganox 1076™ and combinations thereof.

The functional outer layer may suitably be applied on the article in a manner known per se. Preferably a coating composition according to the invention is used. Such composition has been found to result in a coating with advantageous properties.

A functional coating composition according to the invention (for coating an article such as a medical device), comprises b) a functional non-ionic hydrophilic polymer in a total concentration of 0.5-60 wt %, in particular 0.5-30 wt %, based on the total weight of the composition, preferably at least 1.0 in particular at least 2 wt. % more in particular at least 4 wt %, preferably up to 20 wt %, more preferably up to 10 wt %, even more preferably up to 6 wt %.

e) a polyelectrolyte in a total concentration of 0.1-10 wt %, based on the total weight of the composition, in particular 0.1 to 2 wt %, preferably at least 0.5 wt %, preferably up to 1.4 wt % f) a photo-initiator, preferably in a total concentration of 0.1-10 wt. based on the total weight of polymers (hydrophilic polymer b) and ionomer e)

g) optionally a water soluble aliphatic compound (other than the solvent, if that contains an organic alicyclic solvent), a water soluble alicyclic compound (other than the solvent, if that contains an organic alicyclic solvent) or both, in a total concentration of 0.5-25 wt %, based on the total weight of polymers, in particular 1.0-25 wt. %, preferably 2.5-25 wt %, in particular up to 20 wt %, more in particular up to 15 wt %.

h) optionally an antioxidant in a total concentration of 100-10000 ppmw based on the weight of polymers.

Preferably the antioxidant concentration is at least 200, more preferably at least 500 ppmw. Preferably it is up to 5000 ppmw, more preferably up to 2000 ppmw; "ppmw" means parts per million on a weight basis.

Further i) a solvent is typically present, wherein the components b) and e)-h) are dissolved or dispersed. The solvent concentration is usually at least 68 wt %, preferably at least 75 wt %, more preferably at least 80 wt %, even more preferably at least 85 wt % of the total weight of the composition. In view of handling properties (low viscosity) and/or in order to facilitate the application of the composition such that a coating with the desired thickness is obtained, the amount of solvent in the composition is preferably relatively high. For that reason the total solids content is preferably 20 wt % or less.

The solvent may be a single solvent or a mixture. It is chosen such that the polymers can be dissolved or at least dispersed therein. Preferably it comprises water and/or an organic solvent soluble in water, preferably an alcohol, more preferably a C1-C4 alcohol, in particular methanol and/or ethanol. In case of a mixture, the ratio water to organic solvent, in particular one or more alcohols, may be in the range of about 25:75 to 75:25, in particular 40:60 to 60:40, more in particular 45:55 to 55:45.

The concentration of the initiator f) can be determined based upon the efficiency of the initiator, the desired degree of polymerization and the amount of polymer (typically component b) and optionally e)).

Usually, the total initiator concentration is up to 10 wt %, based on the weight of the polymer (sum of b) and c), if c) is a polymer). In particular in case a high dry-out time and/or high lubricity are desired, preferably a relatively low amount is used, in particular an amount of up to 5 wt %, more in particular of up to 4 wt %. Particularly good results have been achieved with an amount of about 3 wt % or less, for instance about 2 wt %.

Usually the concentration is at least 0.1 wt %, based on the weight of the polymer. For improved adhesion a relatively high amount may be used, in particular at least 0.5 wt %, in particular at least 1.0 wt %, more in particular at least 1.5 wt %, for instance about 2 wt %.

As initiator f) preferably a Norrish type II initiator is used. Preferred photoinitiators are water-soluble or can be adjusted to become water-soluble, also preferred photoinitiators are polymeric or polymerisable photoinitiators. Particular good results have been achieved with benzophenone. Other examples of suitable initiators include hydroxymethylphenylpropanone, dimethoxyphenylacetophenone, 2-methyl-l-4-(methylthio)-phenyl-2-morpholino-propanone-1,1-(4-isopropylphenyl)-2-hydroxy-2-methylpropan-1-one, 1-(4-dodecyl-phenyl)-2-hydroxy-2-methylpropan-1-one, diethoxyphenyl acetophenone, and the like. Phosphine oxide photoinitiator types (e.g., Lucirin TPO by BASF) such as benzoyl diaryl phosphine oxide photoinitiators may be used.

The article may be provided with the functional coating composition in any way to provide a layer, e.g. by dipping or spraying, of a suitable thickness.

The composition is usually applied to provide a thickness that is sufficient to impart the desired property (such as sufficient lubricity, sufficient dry-out time). Generally, the dry thickness is at least about 0.1 µm. For increased lubricity/dry-out time the composition may be applied to provide a outer layer having a thickness (in a dry state) of at least 0.5 µm, at least 1 µm or at least 2 µm.

The upper limit is in principle determined by the intended use in combination with the thickness of the primer layer and the relevant dimensions of the article. Generally one may choose the thickness low enough to avoid an unacceptable change in a physical/mechanical property of the article. For instance in case of a catheter for use in the human body the total thickness of the coated catheter (after wetting) should allow insertion into the relevant part of the human, e.g. a blood vessel or urinary track. For a desirable lubricity and/or dry out time an outer layer thickness (in a dry state) of 100 µm or less is generally sufficient. A relatively thin layer, in particular of about 50 µm or less (in a dry state), more in particular of about 30 µm or less may be advantageous with respect to facilitating the curing and/or a particularly low tendency of the coating to delaminate after curing. For a short curing time and/or an advantageous wear resistance the thickness is preferably 20 m or less, more preferably 15 µm or less, in particular 10 µm or less.

In particular in case the article is a medical device for insertion into the body of a human or other animal, such as a catheter, the coating composition is usually applied to provide a total thickness of the coating of up to 100 µm, in particular up to 50 µm, more in particular up to 35 µm, preferably up to 25 µm, in particular up to 15 µm. Very good results with respect to one the one hand a good lubricity and/or dry-out time and on the other hand a good wear resistance and/or advantageously low curing time have been achieved with a coating having a total thickness of about 2-10 µm.

When the coating composition has been applied to the surface it may be cured in any suitable way for the particular initiator and polymer combination.

The invention will now be illustrated by the following examples.

EXAMPLE 1

Urinary Catheter Coating Process

A commercially available medical grade PVC tube (14 french) Raumedic) was used. A mandrel was inserted in the catheter in order to prevent the coating fluid to reach the inside of the catheter and the assembly was then dipped into coating solution 1 or 2 using a Harland PCX coater. Intensity of the lamps was on average 60 mW/cm2 and was measured using a Harland UVR 335 (also known as IL 1400), equipped with an International Light detector SED 005#989. Input optic: W#11521, filter wbs320#27794. The instruction manual of International Light was applied, which is available on the internet: www.intl-liqht.com. The catheter was dipped once for 10 seconds and then cured for 15 seconds with a total dose of 0.9 J/cm2. The catheter was then dipped once into coating solution 3 or 4 for 10 seconds, and cured for 360 seconds at a total dose of 21.6 J/cm2. After drying, the catheter was packed in a 100% humidity environment and sterilized by gamma irradiation.

| Coating solution 1: Primer | |
|---|---|
| Compound | Amount (wt %) |
| PTGL-1000-(TH)2 | 4.25 |
| PVP 1.3 M (K-90) | 0.75 |
| Irgacure 2959 | 0.20 |
| Ethanol | 94.8 |

| Coating solution 2: Primer | |
|---|---|
| Compound | Amount (wt %) |
| PTGL-1000-(TH)2 | 4.50 |
| PVP 1.3 M (K-90) | 0.50 |
| Irgacure 2959 | 0.20 |
| Ethanol | 94.8 |

PTGL-1000-(TH)2 oligomer was synthesised as follows: In a dry inert atmosphere toluene diisocyanate (TDI or T, Aldrich, 95% purity, 87.1 g, 0.5 mol), Irganox 1035 (Ciba Specialty Chemicals, 0.58 g, 1 wt % relative to hydroxy ethyl acrylate (HEA or H)) and tin(II) 2-ethyl hexanoate (Sigma, 95% purity, 0.2 g, 0.5 mol) were placed in a 1 liter flask and stirred for 30 minutes. The reaction mixture was cooled to 0° C. using an ice bath. HEA (Aldrich, 96% purity, 58.1 g, 0.5 mol) was added dropwise in 30 min, after which the ice bath was removed and the mixture was allowed to warm up to room temperature. After 3 h the reaction was complete. Poly(2-methyl-1,4-butanediol)-alt-poly(tetramethyleneglycol) (Hodogaya, $M_n$=1000 g/mol, PTGL, 250 g, 0.25 mol) was added drop-wise in 30 min. Subsequently the reaction mixture was heated to 60° C. and stirred for 18 h, upon which the reaction was complete as indicated by GPC (showing complete consumption of HEA), IR (displayed no NCO related bands) and NCO titration (NCO content below 0.02 wt %). PVP 1.3 is polyvinylpyrrolidone having an average Mv (viscosity related) of 1.3 million (Aldrich).
Irgacure 2359 is also available from Aldrich.

| Coating solution 3: Functional polymer | |
|---|---|
| Compound | Amount (wt %) |
| PVP 1.3 M (K-90) | 5.00 |
| Polyelectrolyte 200.000[1] | 1.25 |
| Benzophenon | 0.12 |
| Glycerol | 0.60 |
| Antioxidant[2] | 2000 ppm on solids |
| $H_2O$ | 46.52 |
| Methanol | 46.52 |

[1]Polyelectrolyte is a polymer of 200.000 Da molecular weight consisting of ionogenic groups being a random copolymer of acrylamide (20%), acrylic acid and sodium salt of acrylic acid (polymer contains 14.5 wt % $Na^+$)
[2]Antioxidant: 3-5'-ditertbutyl-4-hydroxy-benzylalcohol

| Coating solution 4: Functional polymer | |
|---|---|
| Compound | Amount (wt %) |
| PVP 1.3 M (K-90) | 5.50 |
| Polyelectrolyte 200.000[1] | 0.75 |
| Benzophenon | 0.12 |
| Glycerol | 0.30 |
| $H_2O$ | 46.52 |
| Methanol | 46.52 |

All ingredients were commercially obtained

The resultant coatings are found to be lubricious, to have a good dry-out time and adheres sufficiently to the PVC catheter, also after gamma sterilisation. No visible cracks are observed by the naked eye.

The invention claimed is:

1. An article, in particular a medical device, comprising a coating, which coating comprises at least inner and outer layers, wherein
the inner layer is a primer layer, comprising a supporting polymer network which is composed of a supporting polymer selected from the group consisting of polyethers and polythioethers, including copolymers thereof, the supporting polymer network comprising a functional non-ionic hydrophilic polymer entangled in the supporting polymer network; and
the outer layer is a functional layer comprising a functional non-ionic hydrophilic polymer and a polyelectrolyte.

2. An article according to claim 1, wherein the inner and/or the outer layer comprise at least one component selected from the group consisting of water soluble aliphatic compounds, water soluble alicyclic compounds and water soluble antioxidants.

3. An article according to claim 1, wherein
the concentration of the supporting polymer in the primer layer is in the range of 10 to 99 wt %, based on the total dry weight of the of the layer;
the concentration of the functional non-ionic hydrophilic polymer in the primer layer is in the range of 1 to 90 wt %, based on the total dry weight of the layer;
the concentration of the functional non-ionic hydrophilic polymer in the functional layer is in the range of 25 to 99 wt %, based on the total dry weight of the layer;
the concentration of the polyelectrolyte in the functional layer is 1 to 75 wt %, based on the total dry weight of the layer;
the total concentration of the water soluble aliphatic compound and the water soluble alicyclic compound in the functional layer is 0 to 25 wt %, based on the total dry weight of the layer; and
the total concentration of the antioxidant in the functional layer is 0 to 2 wt %, based on the total dry weight of the layer.

4. Article according to claim 1, wherein the dry primer layer has a thickness of 0.1-20 μm, and the dry functional layer has a thickness of at least 0.1 μm, wherein the total dry thickness of the coating is 100 μm or less.

5. Article according to claim 1 selected from the group consisting of catheters, endoscopes and laryngoscopes, tubes for feeding or drainage or endotracheal use, guide wires, condoms, barrier coatings for gloves, wound dressings, contact lenses, implants, extracorporeal blood conduits, and membranes for dialysis, blood filters, and devices for circulatory assistance.

6. A composition for providing an article with a primer layer comprising
a) a supporting polymer selected from the group consisting polyethers and polythioethers, including copolymers thereof, in a total concentration of 1-60 wt %, based on the total weight of the composition
b) a functional non-ionic hydrophilic polymer in a total concentration of 0-30 wt %, based on the total weight of the composition;
c) a Norrish I type photoinitiator, preferably in a total concentration 1-10 wt %, based on the weight of components a) and b); and
d) at least 68 wt % of a solvent, wherein the components a), b) and c) are dissolved or dispersed.

7. A composition according to claim 6, comprising
a) 1-20 wt % of the supporting polymer;
b) 0.3-20 wt % of the functional polymer; and
c) 2-6 wt % based on the weight of components a) and b) of the Norrish I type photoinitiator.

8. A composition according to claim 5, wherein the supporting polymer is selected from the group consisting of copolymers composed of at least a1) a polyether or polythioether; a2) a moiety comprising at least two isocyanates; and a3) a hydroxyalkylacrylate, a hydroxyalkylmethacrylate, a polyhydroxyalkylacrylate and a polyhydroxymethacrylate.

9. A composition or article according to claim 8, wherein a1) is selected from polyalkylene glycols (such as PEG and PPG and combinations thereof) and polytetrahydrofuran; a2) is selected from toluene diisocyanate and 4-cyclohexyldiisocyanate; and a3) is selected from hydroxyethylacrylate and hydroxyethylmethacrylate.

10. A composition or article according to claim 8, wherein the supporting polymer has a number average molecular weight in the range of 300-20000 g/mol.

11. A composition according to claim 5, comprising an organic solvent.

12. A composition for (coating a surface provided with a composition according to claim 5,) comprising:
b) a functional non-ionic hydrophilic polymer in a total concentration of 0.5-60 wt. %, based on the total weight of the composition, e) a polyelectrolyte in a total concentration of 0.1-10 wt %, based on the total weight of the composition, f) a photo-initiatory in a total concentration of 0.1-10 wt, based on the total polymer weight, g) a water soluble aliphatic compound, a water soluble alicyclic compound or both, in a total concentration of 0.5-25 wt %, based on the total weight of polymers h) an antioxidant in a total concentration of 100-10000 ppmw based on the weight of polymers, and i) at least 68 wt % of a solvent, wherein the components b) and e)-h) are dissolved or dispersed.

13. A composition according to claim 12, wherein the polyelectrolyte is an ionomer composed of at least an acrylamide and/or methacrylamide and at least one constitutional unit chosen from the group consisting of an acrylic acid and/or a methacrylic acid; and/or a salt of an acrylic acid and/or a salt of a methacrylic acid.

14. A composition or article according to claim 12, wherein the ionomer has an weight average molecular weight in the range of 20,000 to 2,000,000 g/mol.

15. A composition according to claim 12, wherein the alicyclic compound respectively aliphatic compound is selected from the group consisting of polyols, ethers, aldehydes, amides, esters, thiols, thioesters, organic acids, ketones and combinations thereof.

16. A composition according to claim 12, wherein the antioxidant is an antioxidant selected from vitamin C (ascorbic acid), alkyl hydroxybenzyl alcohols, alkyl hydroxybenzoic acids, pyrogallol, alkylated hydroxytoluene, and 2,6-ditertbutyl-4-ethyl-phenol.

17. An article or a composition according to claim 1, wherein the functional polymer b) is selected from the group consisting of polylactams, polyalkylene oxides, poly vinyl alcohols, polyacrylates, and polyhydroxyalkylates.

18. An article or a composition according to claim 1, wherein the weight average molecular weight of the functional polymer b), is in the range of 20,000 to 10,000,000 g/mol.

19. An assembly, comprising a primer composition according to claim 5.

20. Method for preparing a coating comprising
applying a primer composition to a surface, wherein the primer composition comprises;
  a) a supporting polymer selected from the group consisting polyethers and polythioethers, including copolymers thereof, in a total concentration of 1-60 wt %, based on the total weight of the composition
  b) a functional non-ionic hydrophilic polymer in a total concentration of 0-30 wt %, based on the total weight of the composition;
  c) a Norrish I type photoinitiator in a total concentration 1-10 wt %, based on the weight of components a) and b); and
  d) at least 68 wt % of a solvent, wherein the components a), b) and c) are dissolved or dispersed;
curing the primer composition;
applying a functional coating composition to the surface provided with the primer composition, wherein the functional coating composition comprises;
  e) a functional non-ionic hydrophilic polymer in a total concentration of 0.5-60 wt. %, based on the total weight of the composition,
  f) a polyelectrolyte in a total concentration of 0.1-10 wt %, based on the total weight of the composition,
  g) a photo-initiator in a total concentration of 0.1-10 wt. % based on the total polymer weight,
  h) optionally a water soluble aliphatic compound, a water soluble alicyclic compound or both, in a total concentration of 0.5-25 wt %, based on the total weight of polymers,
  i) optionally an antioxidant in a total concentration of 100-10000 ppmw based on the weight of polymers, and
  j) at least 68 wt % of a solvent, wherein the components b) and e)-h) are dissolved or dispersed; and
curing the functional coating composition.

21. Coating obtained by a method according to claim 20.

22. Article according to claim 1, wherein the primer layer is covalently cross-linked to the functional layer.

* * * * *